United States Patent [19]
Callaway

[11] Patent Number: 5,431,653
[45] Date of Patent: Jul. 11, 1995

[54] KNEE JOINT FLEXION-GAP DISTRACTION DEVICE

[76] Inventor: George H. Callaway, 310 E. 71st St., Apartment 7H, New York, N.Y. 10021

[21] Appl. No.: 88,421

[22] Filed: Jul. 6, 1993

[51] Int. Cl.⁶ .......................................... A61B 17/56
[52] U.S. Cl. .................................................... 606/90
[58] Field of Search ............... 606/90, 86, 89, 99, 606/105, 88, 87, 205, 207; 128/17, 18, 19, 20

[56] References Cited

U.S. PATENT DOCUMENTS

| | | | |
|---|---|---|---|
| D. 262,055 | 11/1981 | Luikart, II | D24/27 |
| 3,750,652 | 8/1973 | Sherwin | 606/90 |
| 3,840,014 | 10/1974 | Ling et al. | 606/90 |
| 3,916,907 | 11/1975 | Peterson | 128/20 |
| 4,066,082 | 1/1978 | Arcan et al. | 606/90 |
| 4,220,146 | 9/1980 | Cloutier . | |
| 4,474,177 | 10/1984 | Whiteside . | |
| 4,501,266 | 2/1985 | McDaniel . | |
| 4,524,766 | 6/1985 | Petersen | 606/88 |
| 4,566,448 | 1/1986 | Rohr, Jr. | 606/88 |
| 4,567,885 | 2/1986 | Androphy . | |
| 4,567,886 | 2/1986 | Petersen . | |
| 4,722,330 | 2/1988 | Russell et al. . | |
| 4,787,383 | 11/1988 | Kenna . | |
| 4,825,857 | 5/1989 | Kenna . | |
| 4,898,161 | 2/1990 | Grundei | 606/105 |
| 4,935,023 | 6/1990 | Whiteside et al. | 606/88 |
| 4,938,762 | 7/1990 | Wehrli | 606/88 |
| 5,053,037 | 10/1991 | Lackey | 606/79 |
| 5,116,338 | 5/1992 | Poggie et al. | 606/90 |
| 5,213,112 | 5/1993 | Niwa et al. | 128/774 |
| 5,234,433 | 10/1993 | Bert et al. | 606/88 |
| 5,263,498 | 11/1993 | Caspari et al. | 128/898 |

Primary Examiner—Stephen C. Pellegrino
Assistant Examiner—Guy V. Tucker
Attorney, Agent, or Firm—Darby & Darby

[57] ABSTRACT

A knee distraction device is provided for use in knee arthroplasty. A mechanism applies an adjustable distraction force between the tibial surface and a point on the distal femur of the flexed knee. The spatial relationship of tibia and femur is allowed to change by rotation of the femur around an axis between the center of the hip and the intercondylar area of the distal femur. As the distraction force is applied, relative tensions in the medial and lateral ligamentous structures of the knee are equalized by changes in the spatial relationship of the femur and tibia. During maintenance of distraction, the posterior femoral bone cut may be positioned at a predetermined distance from the cut tibial surface. The use of this mechanism facilitates accurate sizing of the flexion gap and optimal positioning of knee arthroplasty components.

5 Claims, 5 Drawing Sheets

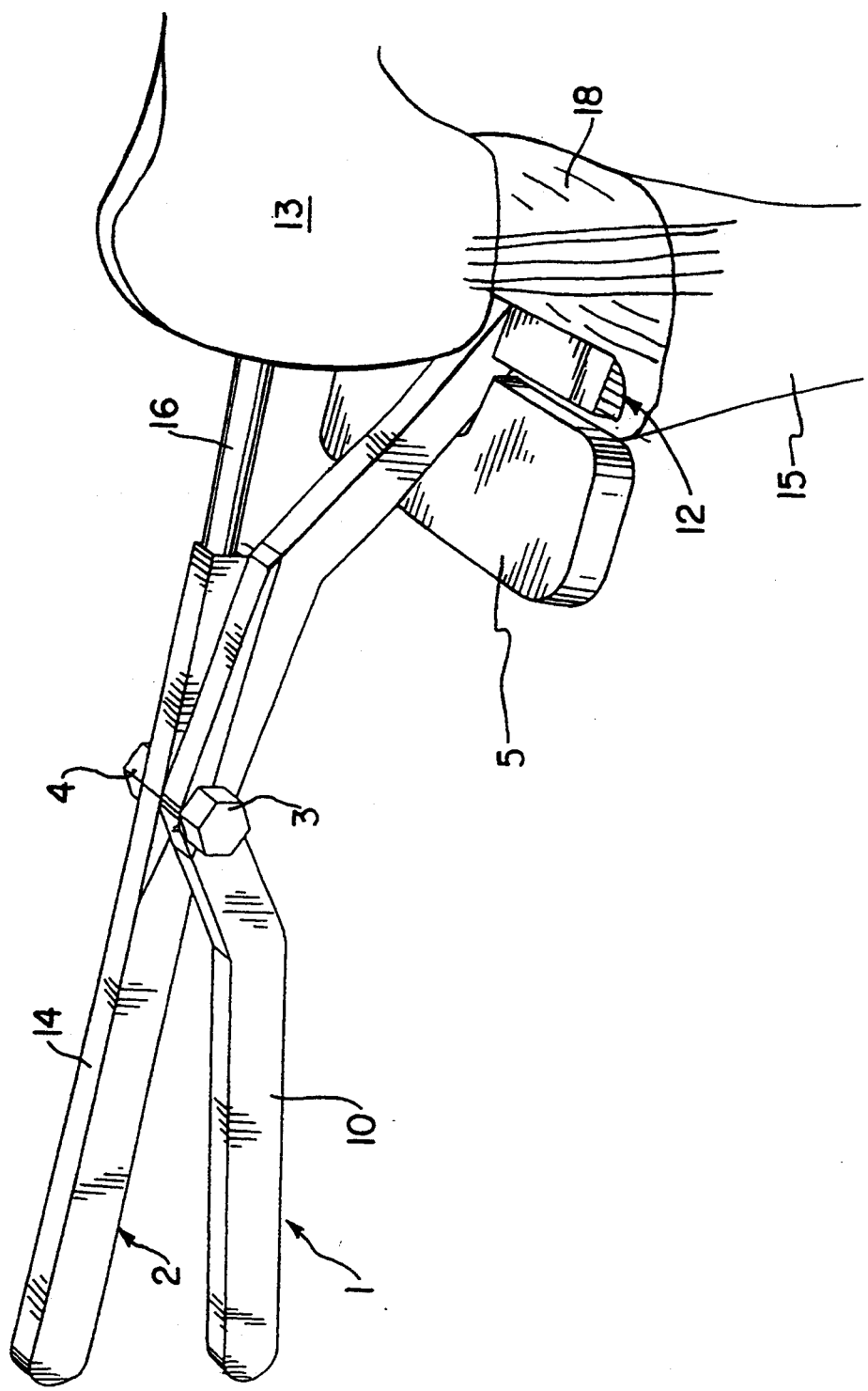

KNEE JOINT FLEXION-GAP DISTRACTION DEVICE

FIELD OF INVENTION

The present invention is a knee joint distraction device for facilitating knee arthroplasty, especially total knee arthroplasty.

DISCUSSION OF PRIOR ART

Primary objectives of knee arthroplasty include restoration of limb alignment, ligament balance, and joint surface contours. Restoration of limb alignment in extension reduces assymetric loading of the bicondylar design, probably reducing the risk of component loosening. Restoration of ligament balance and joint surface contours prevents instability and restores normal joint kinematics.

Surgical instrumentation serves to simplify and standardize the implantation procedure. Several operative techniques have been advocated, differing in instrumentation and in the sequence of bone cuts. The present invention may be usefully employed in any of the several techniques.

Restoration of ligament balance requires careful positioning of the knee arthroplasty components and selective lengthening of contracted ligamentous or soft-tissue structures. Ideally, the ligaments should be balanced at every position of knee flexion. To simplify the surgical technique, the ligament balance is checked mainly at full knee extension and at ninety-degree knee flexion.

Extension balancing. In full extension, both limb alignment and ligament balance must be restored. The distal femoral bone cut is made perpendicular to the axis between the centers of the hip and knee joints. The proximal tibial cut is made perpendicular to the longitudinal axis of the tibial shaft. Contracted ligaments and soft tissues are then lengthened by partial release as needed to equalize their length and tension in extension. After these bone and soft tissue cuts, the gap between distal femur and proximal tibia (the extension gap) should accomodate the combined thickness of tibial and femoral components with the medial and lateral knee ligaments equally tensioned to provide stability.

Historically, ligament balance in extension has been addressed by the use of either spacer blocks or a joint distraction instrument. Spacer blocks are oval, metallic shims of the approximate shape and size of the proximal tibial surface. After proximal tibial and distal femoral cuts are made, spacer blocks of increasing thickness are placed in the extension gap. Gentle medial (valgus) and lateral (varus) stresses are applied to the knee by the surgeon, and the relative lengths and tensions of medial and lateral ligaments are assessed. Incremental releases are performed as needed to balance the ligaments.

In the alternative technique, a joint distraction instrument places is placed between the distal femoral condyles and the previously cut proximal tibial surface during full knee extension. When the force between each condyle and the tibia is equal, tile ligaments are equally tensioned. Partial ligament releases are then performed while maintaining equal ligament tension. When the proper ligament alignment is restored, tile distal femoral cut is made parallel to the proximal tibial cut.

Flexion balancing. In ninety-degrees of knee flexion, ligament balance can be restored by changing the alignment of the posterior femoral bone cut. The tibial cut and soft tissue releases also affect the flexion gap, but these factors are predetermined by the requirements of limb alignment and ligament balance in extension. Historically, the posterior femoral bone cut has been positioned by posterior condyle referencing or by the use of a joint distraction instrument.

Posterior condyle referencing involves empirically positioning the posterior femoral cut to remove slightly more medial than lateral femoral condyle. This external rotation of the cut corrects the most common clinical situation, where the flexion gap is tight medially. However, the posterior condyle referencing technique becomes difficult when the condyles are eroded or when a severe pre-operative deformity exists. Technical errors are possible which may cause malfunction of the implanted knee prosthesis.

A joint distraction instrument places a distracting force between each of the posterior femoral condyles and the previously cut tibial surface during ninety-degree knee flexion. If the force between each condyle and the tibia is equal, the ligaments wiil be nearly equally tensioned. If the extension gap has already been balanced, the position of the posterior femoral cut then be measured from the proximal tibial surface to create a flexion gap of the appropriate size and shape. The joint distraction technique for flexion gap balancing is appealing in theory, but joint distraction instruments in the prior art are difficult to use. Because of shortcomings of instrumentation, many surgeons use the easier but less reliable posterior condyle referencing technique for positioning the posterior femoral bone cut.

U.S. Pat. No. 5,116,338 to Poggie (1992) describes a flexion gap distractor which fits into the space between posterior condyles and tibial plateau. Such prior art devices suffer from a number of disadvantages. The device must be forced into a tight space between the posterior condyles and the tibial plateau. The portions of the device which articulate with the posterior femoral condyles fit poorly with very large and very small knees. Medial and lateral tension adjustments are separate and tactile feed-back of tension is poor, making it difficult to achieve equal tension in the medial and lateral soft-tissues. The size of the device obstructs visualization of the knee joint and obstructs access to the anterior tibial plateau, preventing the use of spacer blocks to position the posterior femoral cut.

U.S. Pat. No. 4,938,762 to Wehrli (1990) describes a flexion gap distractor which attaches to the tibial shaft with a bone screw and engages the femoral intercondylar notch with a bent metallic arm. Such prior art devices also suffer from a number of disadvantages. The need for a screw in an uninvolved and remote portion of the tibia creates undesirable morbidity. The distraction device is free to rotate around the tibial bone screw and therefore does not control medial to lateral motion of the femur relative to the tibia. Such medial or lateral motion can alter the soft-tissue balance in a deceptive manner. Finally, no means is provided for measuring the space between proxmal tibial cut and the proposed posterior femoral cut.

SUMMARY OF THE INVENTION

The present invention concerns an improvement in knee arthroplasty instrumentation, especially applicable to the flexion gap balancing step of implantation. In a preferred embodiment, the invention includes a knee joint distractor which is much simplified in construction and use over the prior art.

The invention allows the application of a distraction force between the tibia and a single point near the intercondylar notch of the distal femur of the flexed knee. The femoral contact point is maintained in a fixed medial to lateral position relative to the tibia. The femur is allowed to rotate on an axis between the hip joint and the area of the intercondylar notch. When the distraction force is applied, the femur rotates until the medial and lateral ligaments of the knee are equally tensioned.

During maintenance of distraction, a guide or spacer block may be used to place the posterior femoral cut at a predetermined distance from the cut tibial surface. By this technique, the size and shape of the flexion gap may be accurately matched to the thickness of the arthroplasty implant. The use of a spacer block is appealing, because the same spacer block can be used to measure both extension and flexion gaps. This reduces the number of instruments and makes the procedure more intuitive.

OBJECTS AND ADVANTAGES

Accordingly, several objects and advantages of the present invention are:
(a) to provide a means for tensioning equally the medial and lateral ligaments and soft tissues of the flexed knee while controlling the medial to lateral relationship of the femur and tibia;
(b) to provide a means for positioning the posterior femoral cut during total knee arthroplasty in a manner which creates a flexion gap of predetermined size and shape;
(c) to provide an instrument for flexion gap distraction which is simplified in design and use relative to prior art;
(d) to provide an instrument for flexion gap distraction which may be operated with one hand, which may be advantageous in a surgical procedure;
(e) to provide an instrument for flexion gap distraction which is less bulky than prior art and which therefore allows improved visualization of the knee during distraction;
(f) to provide an instrument for flexion gap distraction which allows access to the anterior portion of the cut tibial surface during distraction, thereby making it possible to use a spacer block or other measuring devices to position the posterior femoral cut at a predetermined distance from the cut tibial surface;
(g) to provide an instrument for flexion gap distraction which provides tactile feedback regarding soft tissue tension through a hand-held squeeze grip.

Still further objects and advantages will become evident from a consideration of the ensuing description and drawings.

BRIEF DESCRIPTION OF THE DRAWINGS

FIG. 5 shows a typical embodiment of the present invention on a flexed knee after application of a distraction force, used in combination with a spacer block to position the posterior femoral cut at a predetermined distance from the cut tibial surface.

DESCRIPTION OF INVENTION

Figure 1:
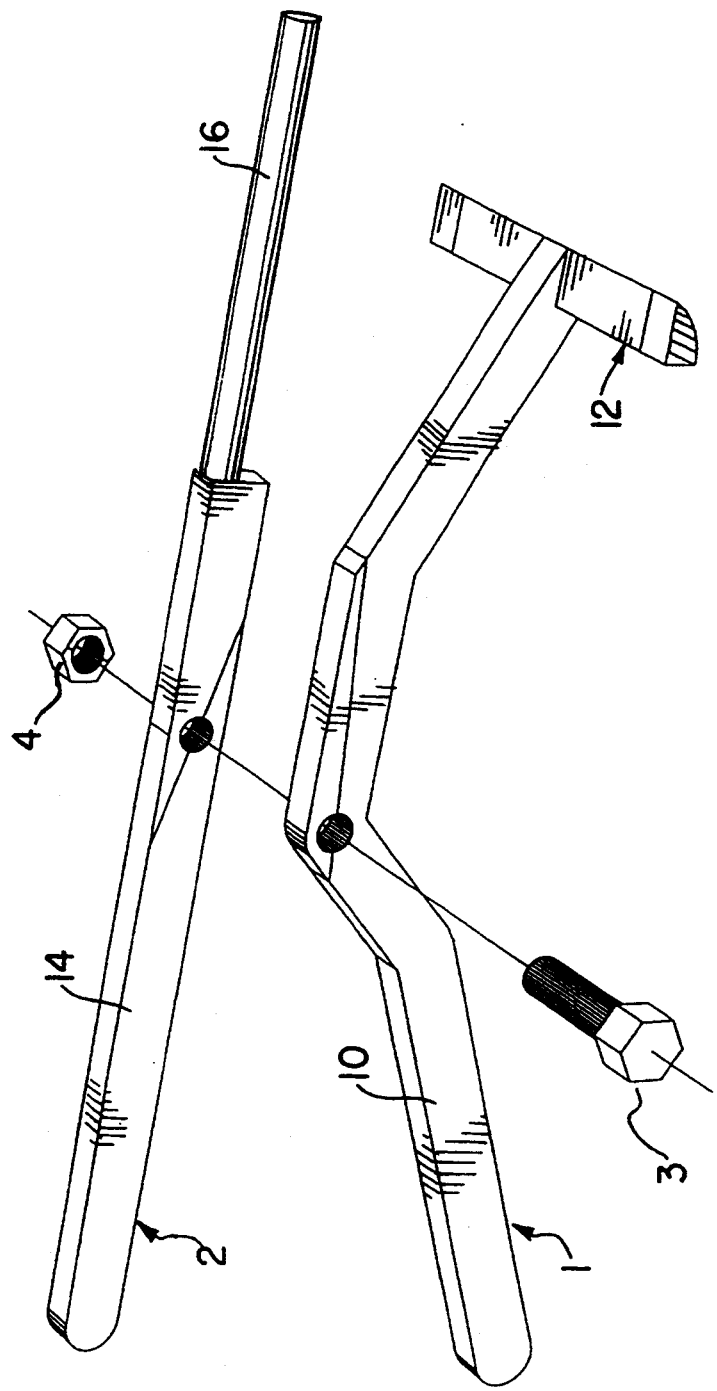
FIG. 1 shows a perspective view of the components of a preferred embodiment of a knee flexion gap distraction device according to the present invention.
Figure 2:
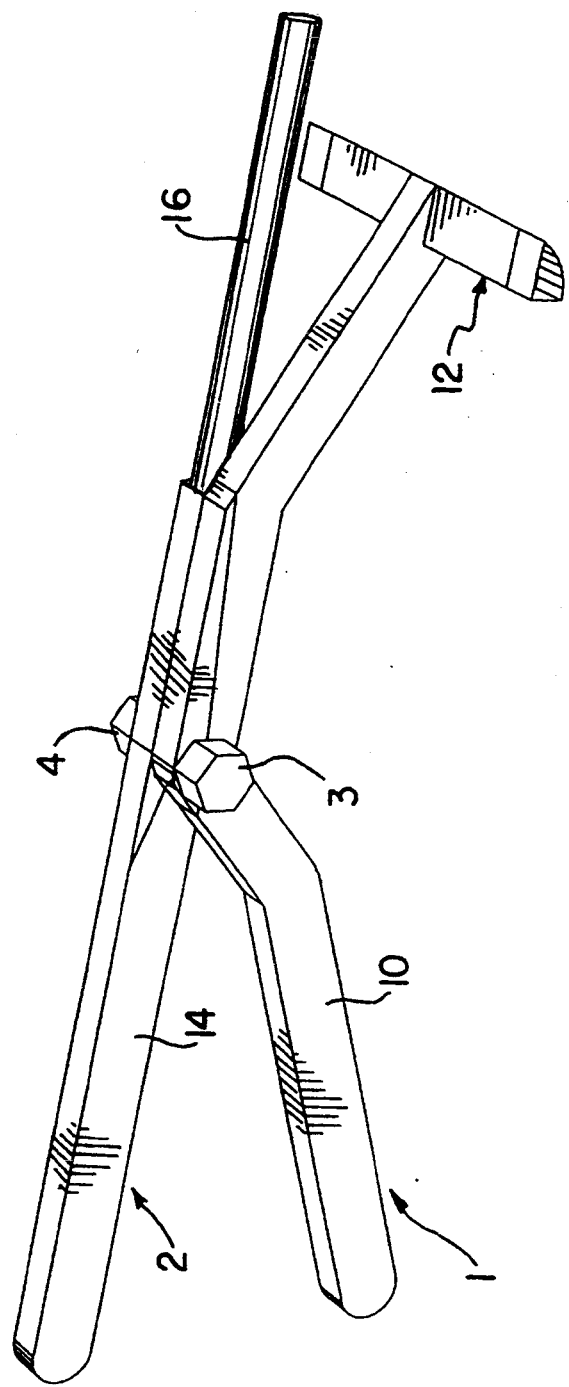
FIG. 2 shows a perspective view of the assembled components of FIG. 1.

A typical embodiment of the knee flexion gap distraction device is illustrated in FIGS. 1 and 2. The femur is shown at 13 and the tibia at 15. The present invention includes a tibial device 1 with a contoured handle 10 and a broad, T-shaped platform 12 on the opposite end. A femoral device 2 has a contoured handle 14 and a cylindrical opposite end 16. Tibial device 1 and femoral device 2 are pivotally joined by a bolt 3 and nut 4 to form a hinge.

Figure 3:
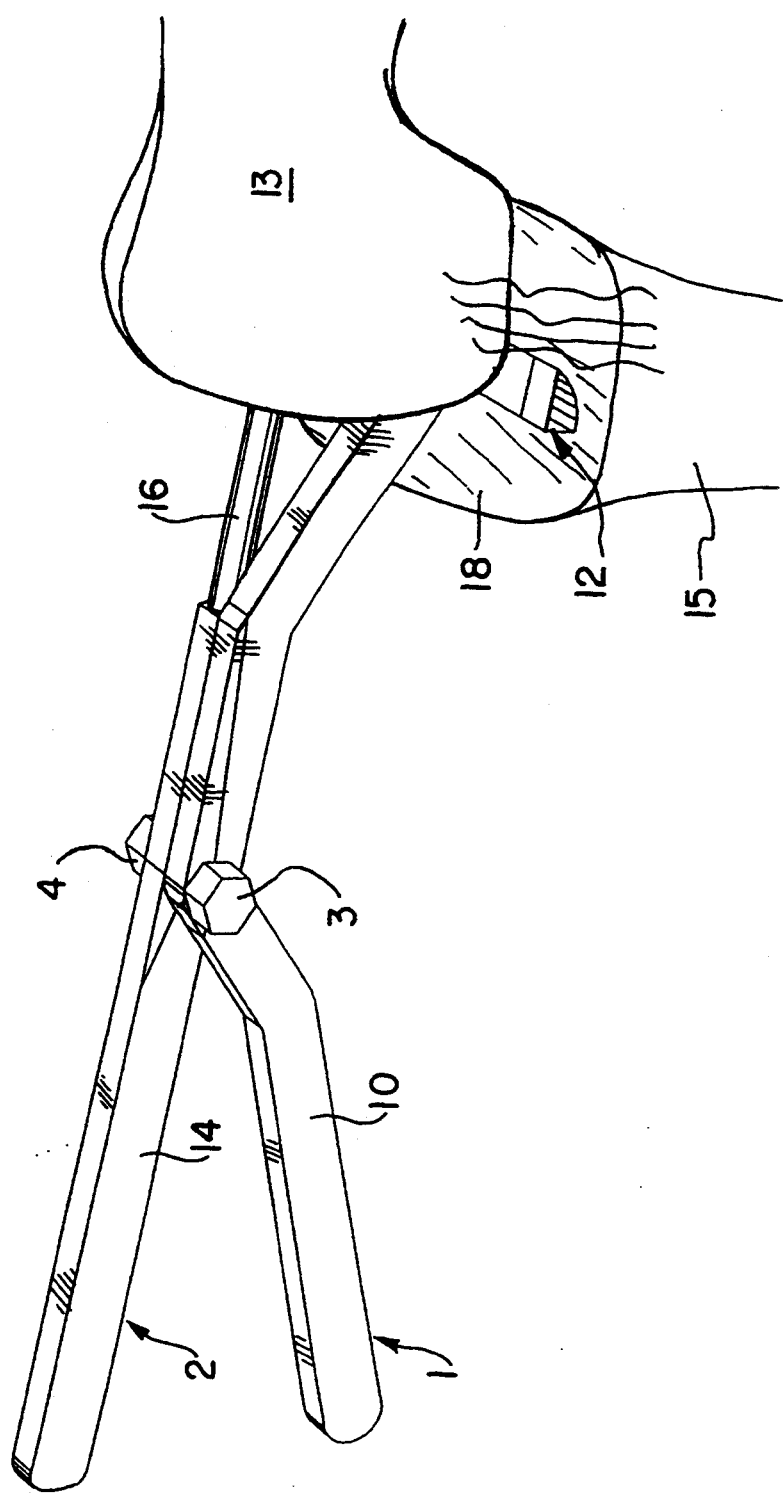
FIG. 3 shows a typical embodiment of the present invention on a flexed knee before application of a distraction force.
Figure 4:
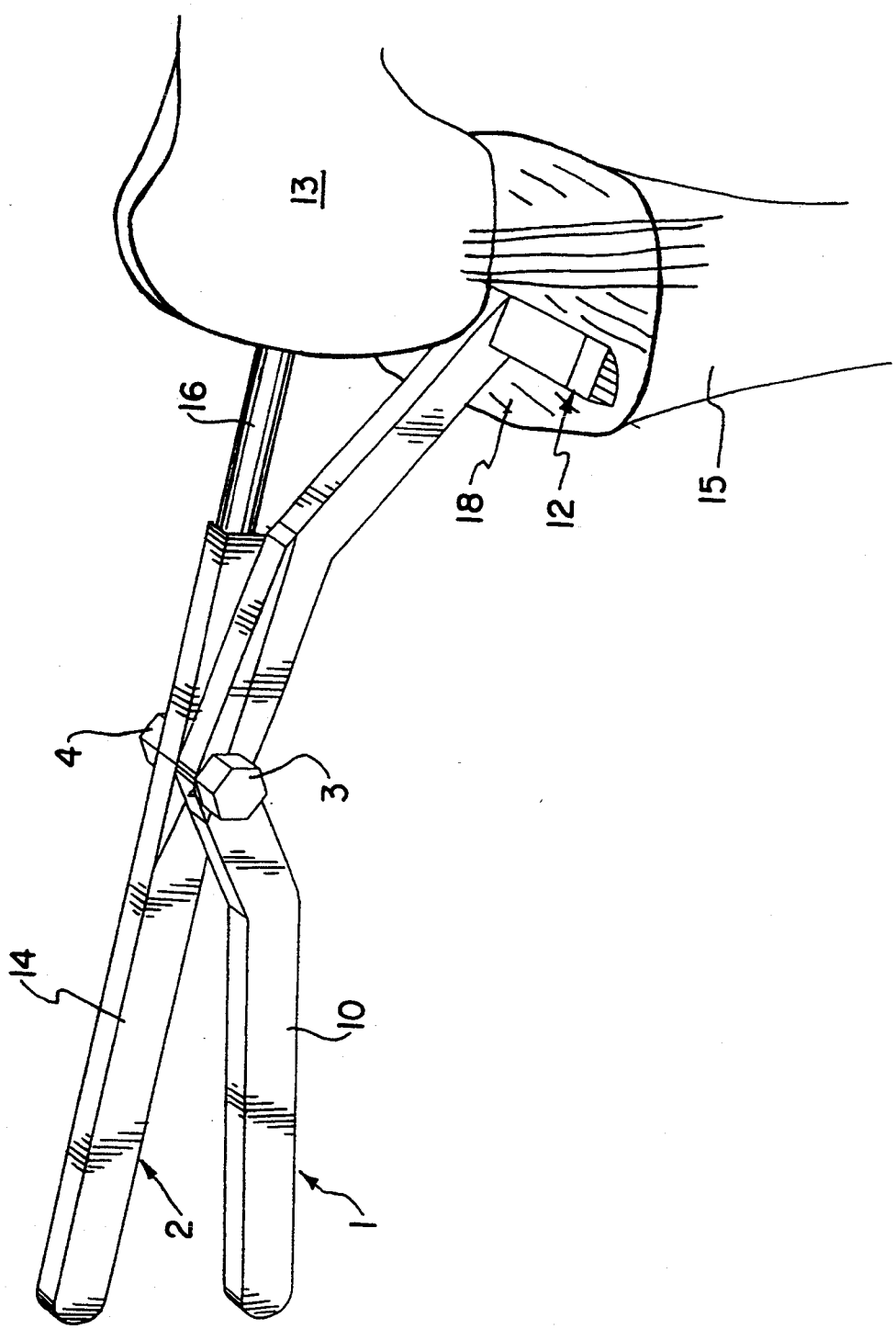
FIG. 4 shows a typical embodiment of the present invention on a flexed knee after application of a distraction force.

FIGS. 3, 4, and 5 show one use of the knee flexion-gap distraction device. The T-shaped platform 12 of tibial device 1 is placed in the center of the cut tibial surface 18, with the knee flexed to ninety-degrees. The cylindrical end 16 of femoral device 2 is inserted into a pre-drilled opening (not shown) which leads from the center of the femoral intercondylar notch into the femoral intramedullary canal. The contoured handles 10 and 14 of tibial device 1 and femoral device 2 together form a hand-grip which, when squeezed, applies a distraction force between the distal femur and proximal tibial surface.

The T-shaped platform 12 of tibial device 1 maintains the distal femur centered above the tibia in a medial to lateral direction. The cylindrical end 16 of femoral device 2 lifts the distal femur away from the tibial surface 18 while allowing rotation of the femur 13 around an axis connecting the hip joint and the hole in the intercondylar area of the distal femur into which femoral device 2 is inserted.

Rotation of the femur around this axis allows approximate equalization of tension applied to the medial and lateral ligaments. Tactile feedback through the hand-held squeeze grip or direct palpation of the knee ligaments will help determine the appropriate amount of distraction force. During maintenance of the distraction force, the optimal anterior-posterior positioning of the femoral component may be measured directly from the cut surface of the tibia.

A spacer block 5 may be placed on the cut tibial surface and used to determine the correct position of the posterior femoral cut. Alternatively, the spacer block 5 could be used as a tibial platform for the knee flexion gap distraction device, with the spacer block 5 and distraction device linked together.

The present invention has significant advantages over the prior art. When compared to other joint distractors, the use of femoral rotation to equalize tension among the ligaments eliminates the need for separate distractors for each condyle, thereby greatly simplifying instrument construction and use. When compared to tile posterior condyle referencing technique, ligament balancing is more reliable and reproducible, especially in cases of condylar erosion and pre-existing deformity.

While the above description contains many specificities, these should not be construed as limitations on the scope of the invention, but rather as an exemplification of one preferred embodiment thereof. Many other variations arc possible. For example, the method of engaging the distal femur may be modified to form a which engages the femoral intercondylar notch or modified to form a linkage between an intramedullary rod and the distraction device. The method of engaging the proximal tibia may take the form of a platform or intramedullary rod. The methods of applying, measuring, or maintaining the distraction force may include springs, ratchets, suspended weights, strings, elastic bands, screws, or gear mechanisms. The methods of positioning the posterior femoral cut relative to tibial reference points may include separate measuring devices, extensions of the tibial portion of the distraction device, or guides which arc positioned relative to the tibia or the tibial portion of the distraction device. Accordingly, the scope of the invention should be determined not by the embodiments illustrated but by the appended claims and their legal equivalents.

I claim:

1. A flexion-gap distraction device for use in positioning the femoral and tibial components of a total knee in a total knee arthroplasty, comprising first and second levers pivotally connected at a point intermediate their ends, said first lever including means at its forward end for engaging the distal end of the femur of a flexed knee such that the femur may rotate about an axis extending between the center of the hip joint and the femoral intercondylar notch area, and said second lever being connected to a transverse member at its forward end for engaging the tibial platform, whereby pressure applied to the rearward ends of said lever distracts the distal end of the femur and the tibial platform so that the patients medial and lateral knee ligaments may be equally tensioned in flexion.

2. A flexion-gap distraction device according to claim 1, wherein said transverse member includes a curved surface which is adapted to engage the tibial platform.

3. A flexion-gap distraction device according to claim 1, wherein said levers are pivotally connected such that a force tending to push the rearward ends of the levers together tends to separate the forward ends of said levers.

4. A flexion-gap distraction device according to claim 1, wherein said means at the forward end of the first lever comprises a rod like member adapted to be received within a complementary bore within the femur.

5. A flexion-gap distraction device according to claim 4, wherein said levers are pivotally connected such that a force tending to push the rearward ends of the levers together tends to separate the forward ends of said levers.

* * * * *